United States Patent [19]

Anagnostopoulos

[11] 4,273,877
[45] Jun. 16, 1981

[54] SPIRAL PLATING APPARATUS

[75] Inventor: Gerasimos D. Anagnostopoulos, Twickenham, England

[73] Assignee: National Research Development Corporation, London, England

[21] Appl. No.: 47,478

[22] Filed: Jun. 11, 1979

[30] Foreign Application Priority Data

Jun. 13, 1978 [GB] United Kingdom ............... 26794/78

[51] Int. Cl.³ ............................................. C12M 1/32
[52] U.S. Cl. ..................................... 435/293; 435/292
[58] Field of Search .......................... 435/30, 292, 293; 141/94, 95, 96, 198

[56] References Cited

U.S. PATENT DOCUMENTS

| 3,778,351 | 12/1973 | Rosov | 435/293 |
| 3,799,844 | 6/1979 | Campbell et al. | 435/292 |
| 3,850,754 | 11/1974 | Wilkins et al. | 435/30 X |
| 3,892,632 | 7/1975 | Campbell et al. | 435/30 |
| 3,962,040 | 6/1976 | Campbell et al. | 435/291 |

FOREIGN PATENT DOCUMENTS 1389254 3/1975 United Kingdom ..................... 435/292

OTHER PUBLICATIONS

R. E. Trotman, "The Automatic Spreading of Bacterial Culture over a Solid Agar Plate," Journal of Applied Bacteriology, vol. 34, No. 3, pp. 615-616; 1971.

L. S. Gall et al., "Partially Automated System for Microbiological Analysis," Developments in Industrial Microbiology, vol. 11, pp. 460-469; 1970.

Primary Examiner—Robert J. Warden
Attorney, Agent, or Firm—Lowe, King, Price & Becker

[57] ABSTRACT

The invention relates to apparatus for spiral plating of microorganisms on a growth medium for making a viable cell count. The apparatus comprises means (2) for rotating a plate (3) containing growth medium, an inoculator (7) adapted to expel inoculum onto the growth medium, means (8) for moving the inoculator along a radius of the plate as the plate rotates so as to deposit inoculum along a spiral path on the growth medium, means for exerting a force on the inoculator such that the inoculator can continuously keep contact with and follow contours on the growth medium, and means (4) for controllably varying the rate of expulsion of inoculum along the spiral path. The invention also relates to an improved inoculator assembly, apparatus for controllably varying the rate of depression of a syringe plunger, and a surface sensor assembly for use in a spiral plating apparatus. When the spiral has been completed, the plate is incubated and the resulting colonies are counted in a suitable area of the plate. The viable cell count can then be calculated.

20 Claims, 13 Drawing Figures

SPIRAL PLATING APPARATUS

This invention relates to apparatus for making a viable count of microorganisms, and more particularly to spiral plating apparatus.

Viable cells can only be differentiated from nonviable cells by evidence of growth. If bacterial cells are seeded in or on a solidified agar medium, they become immobilised and when growth conditions are established each individual cell gives rise to a visible colony of progeny cells. Each colony, therefore, represents one parent cell and the number of parents is found by counting the colonies.

Each agar plate (9 cm in diameter) can accomodate up to 300 colonies if their counting is to be considered statistically significant. The inoculum that can be spread over the surface of an agar plate can only be a small fraction of one milliliter (ml). Therefore, when the viable population in a suspension is not known and can be up to $10^7$ cells/ml, up to 5 serial decimal dilutions in a suitable diluent are carried out, and no ideal diluents have been established in all instances. Furthermore, each of these dilutions has to be plated, so that after incubation one plate within the desirable colony range is chosen for counting, and the remainder are discarded. This traditional method is time-consuming, wasteful of materials and subject to experimental error.

A method of spiral plating on a single agar plate has been proposed and is described for example, by R. E. Trotman in J. appl. Bact. 34 (3), 615-616 (1971). Improvements in the basic concept of spiral plating are described by Campbell and Gilchrist in U.S. Pat. Nos. 3,799,844, 3,892,632 and 3,962,040. According to these patents, reducing amounts per unit of length of an undiluted microbial suspension are distributed along a spiral track on an agar plate. As an agar plate rotates an inoculator moves along a radius of the plate and thereby describes a spiral track. The rate at which the inoculator releases inoculum on to the agar surface is reduced in a predetermined way. The inoculum is dispensed from a syringe, the plunger of which engages with one end of an arm. In operation, the other end of the arm slides down a curved surface and the changing speed of sliding of the arm effects a reducing speed of inoculum syringe operation. By this method, the reduction of inoculum per unit length of track can be controlled resulting in a constantly reducing concentration range on a single plate. After incubation, colonies are observed along the spiral track. Where the inoculator has moved from near the centre to the periphery of the plate the spacing between colonies along the track increases from the centre to the edge. Well spaced colonies along a portion of the spiral are counted and the result is divided by the volume of sample contained in that area. This volume can be determined by calculation.

The present invention is concerned with improvements in the system described above.

According to one aspect of the present invention, there is provided apparatus for spiral plating of microorganisms on a growth medium for making a viable cell count, which comprises means for rotating a plate containing growth medium, an inoculator adapted to expel inoculum onto said growth medium, means for moving said inoculator along a radius of said plate as said plate rotates so as to deposit inoculum along a spiral path on said growth medium, means for exerting a force on said inoculator such that said inoculator can continuously keep contact with and follow contours on said growth medium, and means for controllably varying the rate of expulsion of inoculum along said spiral path.

In another aspect, the invention provides an inoculator assembly for use in a spiral plating apparatus, comprising an inoculator holder, a pivot on said inoculator holder, an arm mounted to balance on said pivot, an inoculator mounted on said arm and adapted to pass over a growth medium to be inoculated, and means for exerting a force on said arm such that said inoculator can continuously keep contact with and follow contours on said growth medium.

In a further aspect, the invention provides apparatus for controllably varying the rate of depression of a syringe plunger, comprising a syringe, a plunger slidable within said syringe, a rotatable member having a curved surface in driving engagement with said plunger, and means for rotating said rotatable member whereby said plunger is depressed at a rate varying according to the curvature of said curved surface.

In addition, the invention provides a surface sensor assembly for use in a spiral plating apparatus, comprising a probe adjustable in height, an inoculator holder adjustable in height, and a pair of indicators respectively on said probe and on said inoculator holder arranged so that, when said probe is adjusted to contact a growth medium, and said inoculator holder is adjusted until said indicators are in a predetermined relative position, said inoculator holder is at a suitable height for inoculum to be distributed on the growth medium.

Preferred embodiments of the invention will now be described with reference to the accompanying drawings, in which.

Figure 1:
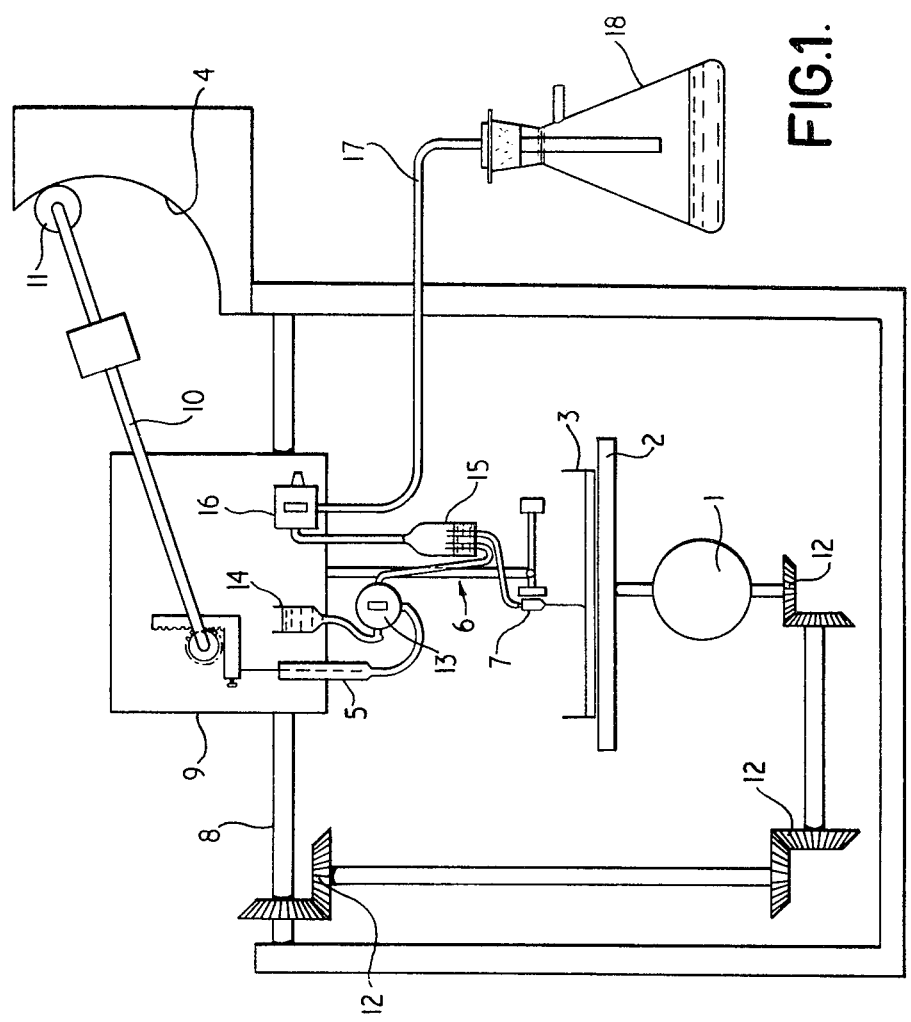
FIG. 1 is a simplified diagram of spiral plating apparatus according to an embodiment of the invention.

Referring to FIG. 1, a reversible electric motor 1, capable of 85 rpm, drives a rotating table 2 on which an agar plate 3 is fastened so that it rotates with the table. Inoculum is inoculated onto the agar by means of an inoculator 7 held in a vertically-adjustable inoculator holder 6. Inoculum is controllably expelled from the inoculator by a continuous unbroken paraffin oil column extending between the inoculator and a microsyringe 5. Expulsion of inoculum is described in more detail with reference to FIG. 4. The microsyringe 5 communicates through a first 3-way valve 13 (paraffin oil valve) to a paraffin oil reservoir 14, and through a vial 15 with the inoculator 7. The vial 15 also communicates, through a second 3-way valve 16 (vacuum valve) with a vacuum line 17, through an effluent flask 18. The vacuum line suitably operates at 500 ml/min. The inoculator holder 6 is adjusted according to the agar thickness on the plate, as described below with reference to FIG. 3. The inoculator assembly 5, 6, 7 is supported on a stage 9 which is moved linearly by a screw 8 which transforms the motor revolutions through gears 12. The plunger of the microsyringe 5 is engaged to an end of an arm 10. In use, the other end of the arm 10 slides, by means of a terminal roller 11, down a computer-produced 4-log curve 4 in a metal plate. Thus, as the agar plate 3 rotates and the inoculator moves along a radius from the centre to the outside of the plate, the rate of operation of the microsyringe plunger is gradually reduced.

Figure 5:
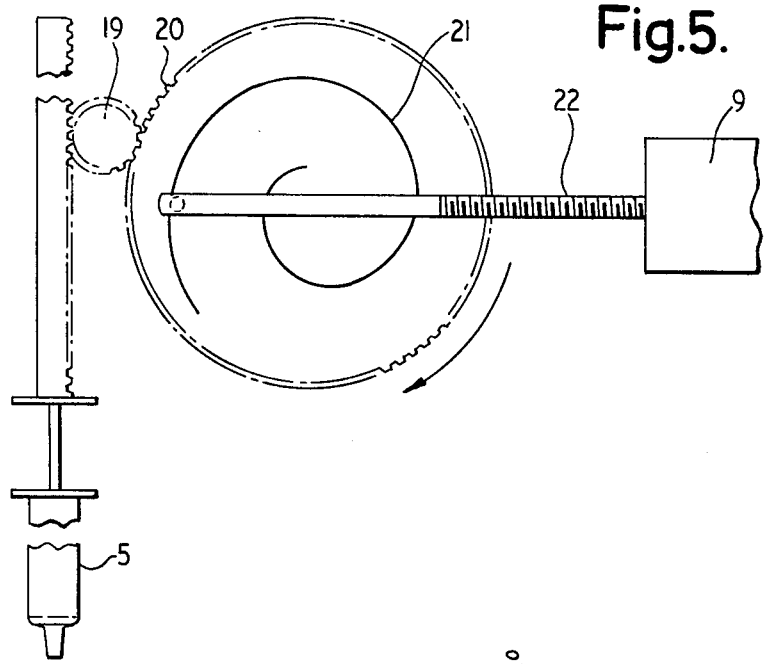
FIG. 5 shows an alternative microsyringe mechanism.

An alternative mechanism for operating the microsyringe, in place of the curve 4 and arm 10, is shown in FIG. 5. The plunger of the microsyringe 5, having a toothed rack joined thereto, is driven by a toothed wheel 19 which in turn is driven by a circular toothed plate 20. The plate 20 has an abutment 21 in the shape of an Archimedes spiral. The abutment 21 may be a shoulder on the plate or a groove in the plate, and engages with the end of a rod 22 which is fixed to the moving stage 9 (see FIG. 1). The plate 20 is spring-loaded and tends to turn in the direction shown by the arrow, but is held up by the rod 22 which acts as a brake. As the rod moves linearly with the moving stage 9, it releases the block on the plate rotation. This rotation is transmitted to the syringe plunger. The plunger therefore moves similarly to the plunger in FIG. 1 which is actuated by the curve and arm. When the electric motor 1 is reversed, the plate 20 of FIG. 5 is rewound. The arrangement of FIG. 5 provides the possibility of reversing the process employed in FIG. 1, i.e. instead of initiating the inoculation of the agar plate 3 with a high deposition of inoculum, it is possible to start at a minimal inoculum which increases gradually with the progression of the spiral. This has the advantage of excluding carry-over of inoculum from heavily inoculated to lightly inoculated areas.

Figure 2:
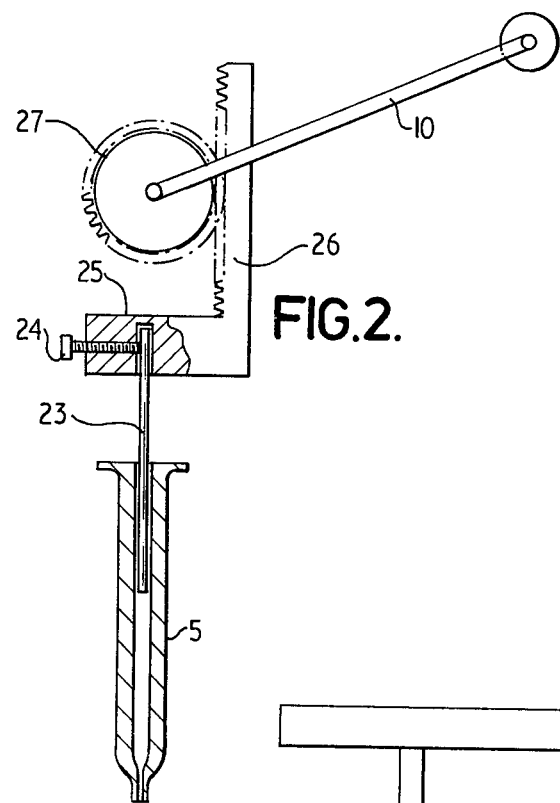
FIG. 2 shows the microsyringe mechanism of FIG. 1.

FIG. 2 shows the mechanism by which the microsyringe 5 of FIG. 1 operates. The microsyringe is, for example, of 0.05 ml capacity. The microsyringe 5 is actuated by a plunger 23. The plunger is fixed by a screw 24 to a plunger depression table 25, which forms the horizontal limb of an L-shaped member. The vertical limb is a toothed rack 26 which engages with a toothed wheel 27 fixed on the lower end of the arm 10. As the arm 10 falls down the curve 4, the toothed wheel 27 rotates clockwise and drives the toothed rack 26 downwards. The plunger 23 is thus moved downwards, expelling paraffin oil from the microsyringe 5 and hence inoculum from the inoculator 7.

Figure 3:
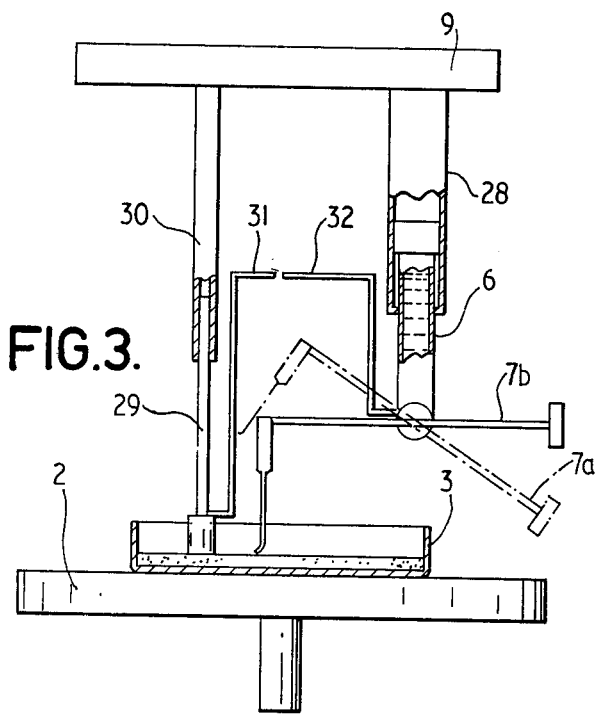
FIG. 3 shows a surface sensor assembly for positioning of an inoculator.

FIG. 3 shows a surface sensor assembly for positioning of the inoculator. A disadvantage of previously proposed inoculator systems is that they required pouring of plates on an even, level surface with a constant quantity of agar medium. The mechanism of FIG. 3 enables the inoculator to be positioned correctly whilst it is in a non-operative position. The instrument can therefore be used with varying thickness of plate and of the agar medium. The agar plate 3 to be inoculated is placed on the rotating table 2. The inoculator holder 6 is vertically adjustable inside a sleeve 28 which is fixed to the underside of the stage 9. A probe 29 is also vertically adjustable inside another sleeve 30 fixed to the underside of the stage. The inoculator 7 is pivoted to the lower end of the inoculator holder 6 and movable between a non-operative position 7a and an operative position 7b. The probe 29 and the inoculator holder 6 are provided with height indicators 31 and 32, respectively. With the inoculator in the non-operative position 7a, the probe 29 is adjusted until it just touches the agar surface. The inoculator holder 6 is then adjusted until the indicators 31 and 32 are in line. In this position, the inoculator is at the correct height above the agar medium. The probe 29 is then retracted and the inoculator moved to the operative position 7b. A screw mechanism (not shown) is provided for fine height adjustment of the inoculator.

Figure 4:
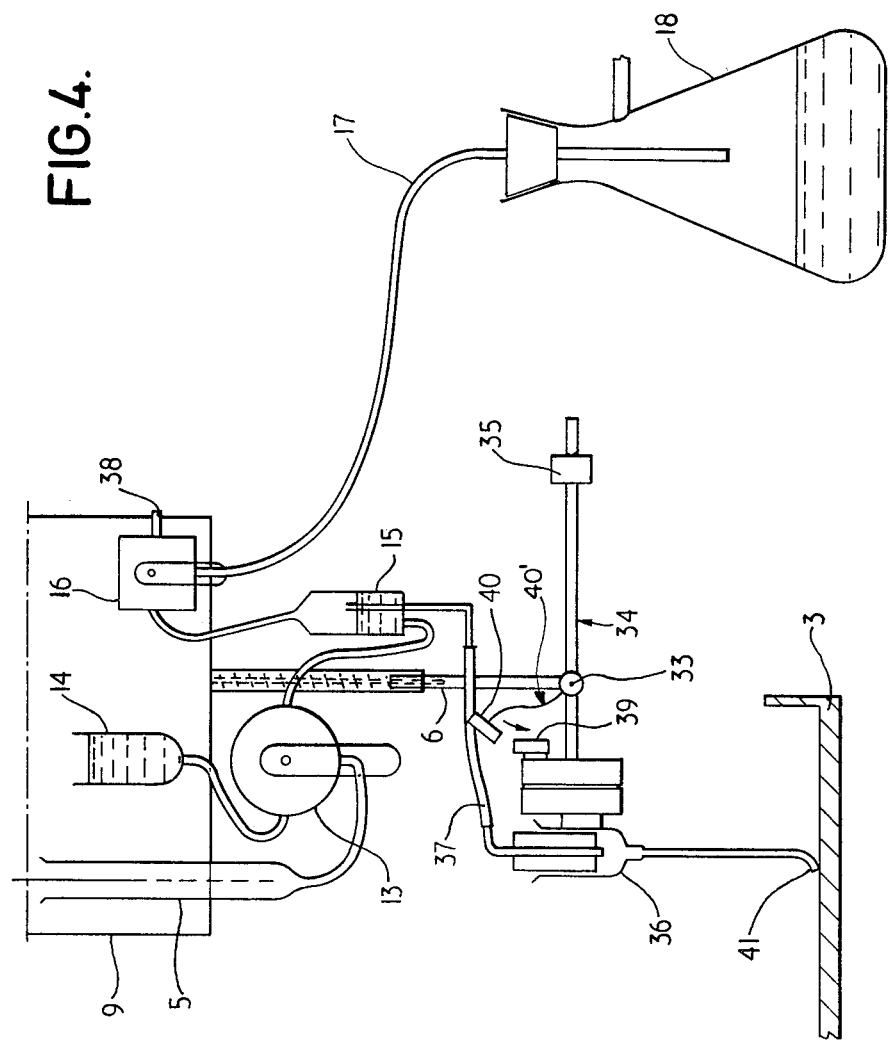
FIG. 4 shows an inoculator assembly.

The inoculator assembly of FIG. 1 is shown in more detail in FIG. 4. The inoculator holder 6 is vertically adjustable and has a horizontal pin 33 at its lower end. The inoculator comprises a horizontal arm 34 which freely balances on the pin 33 as a pivot. A weight 35 can be slid along the arm 34 to aid balancing. The operative part of the inoculator is a hypodermic needle 36, which is curved at its tip 41. The reservoir of the needle 36 is plugged and communicates, through a flexible tube 37, with the vial 15. The 3-way vacuum valve 16 has connections to the vial 15, the vacuum line 17 and the atmosphere 38. The 3-way paraffin oil valve 13 has connections to the microsyringe 5, the paraffin oil reservoir 14 and the vial 15. The microsyringe, the paraffin oil reservoir, the vial and the two 3-way valves are all supported by the stage 9.

A first magnet 39 is fixed to the arm 34 adjacent the needle 36. A second magnet 40 is fixed to the inoculator holder 6, as by wire 40', shown in FIG. 4. The magnets are arranged to repel each other, ensuring a gentle downwards force on the inoculator. The needle 36 thus makes a continuous skiing contact with the agar, following the contours of the agar surface irrespective of the level to which agar has been poured and the degree of dryness and surface wrinkling. The open tip of the needle is slightly flattened so that, instead of being circular, it is elliptical with a horizontal major axis transverse to the spiral path. This assists the skiing contact with the agar and ensures that inoculum is planted on the agar immediately it appears at the tip of the needle. When plating has been completed, the inoculator is moved to its non-operative position 7a (see FIG. 3) by manually overriding the repulsion between the magnets 39 and 40.

Before loading the needle with inoculum, a continuous bubble-free liquid column is established betwen the tip of the needle and the microsyringe, using paraffin oil for the syringe and its connection with vial 15 and either sterile water or the actual inoculum for the rest of the system between the tip of the needle and the vacuum valve 16. This condition is easily obtained within a few seconds, by means of the paraffin oil valve 13 and the vacuum valve 16.

Each time the arm slides down the curve and the toothed wheel depresses the syringe plunger, a fixed inoculum is expelled from the tip of the needle and an equal volume of paraffin oil enters vial 15 visibly. On completion of plating, this oil needs replacement from the reservoir 14. This is done by connecting the syringe with the reservoir (valve 13) and lifting the arm to the starting position before the reversion of the stage 9.

On establishing a bubble-free continuous liquid line between syringe and inoculator tip, any minute movement of the microsyringe plunger has an immediate response at the tip of the needle owing to the incompressibility of the liquid line. Therefore, success depends on tightness of connections.

It should be noted that the microsyringe never comes into direct contact with the inoculum, in contrast to previous models. Therefore, the syringe is never littered with fatty layers etc. and thus its sensitivity is preserved. Furthermore, a bacteriological grade of paraffin oil, previously sterilised, is an inert liquid from the point of view of microbial growth and antimicrobial activity.

A further advantage of the above arrangement, which is not shared by previous models, is that once the system is filled with inoculum, more than one plate can be plated in succession. This is an important feature when it is desirable to plate different selective and differential media or when it is intended to test the inhibitory action of different agents incorporated in the medium of several plates.

Decontamination of the system is operated in situ. The following practice has been found satisfactory for decontamination of the system from $10^9$ cells/ml of Serratia marcescens without residual inhibitory activity left in the system:

Hycolin 5% (v/v), 1 ml, is sucked into the system and left for 5-10 seconds; then the system is washed using 10 ml water. This treatment makes the system ready for next inoculation. Occasional washing of the system with a detergent solution is also practised, in order to extend the life of the needle and avoid deposition of fat etc. in the system.

Owing to its sensitive function, particularly when the inoculum release rate becomes a minute fraction of ml/cm, the inoculator has some features of high importance. Its weight is perfectly balanced at the pin 33 and it is freely rotatable about this pin. Agar plates have to be dried before use and this causes irregularities on the agar surface. If the inoculator rested on the agar surface under its own weight, it would jump over the irregularities, resulting in uninoculated areas and uncontrolled damage of the medium. With the arrangement of FIG. 4, the inoculator rests on the agar medium gently by virtue of the repulsion between the two magnets 39 and 40. This secures uninterrupted contact of the tip 41. The tip of the needle skis over the agar irregularities so that the needle does not harm the medium. The hypodermic needle 36 can either be rejected after use if it is disposable or it can be re-used.

When the spiral has been completed, the plate is incubated and the colonies are counted. The total amount of inoculum on the plate and the rate of reduction of expulsion of inoculum are known, and so is the amount of inoculum received by each of the grooves. The volume of inoculum in any area of the plate can then be calculated. If the colonies within that area are counted, the viable cell count can be found. The following procedure is described in more detail purely by way of example, and it will be appreciated that other counting procedures are possible.

Figure 6:
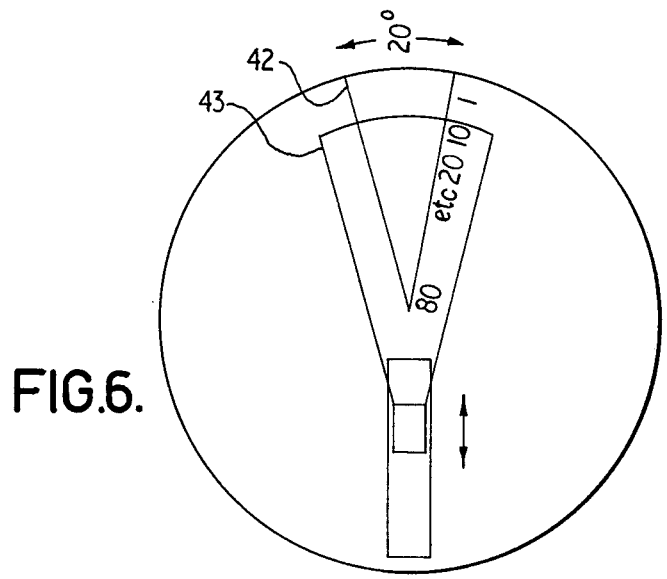
FIG. 6 shows apparatus used during counting of the plates.

As shown in FIG. 6, a plastic transparent plate has been made to show the spiral pattern produced by the tip of the inoculator on the agar surface for a 1200 cm spiral and 80 grooves. If this plate is placed on the underside of an agar plate over a light source and with the aid of $\times 5$ to $\times 10$ magnification, allocation of colonies per groove can easily be decided.

The plastic plate (grid) has a 20° sector 42 marked from its centre and a mobile mask 43 that leaves uncovered that peripheral concentric part of the sector where counting of colonies is desired. The number of grooves, counting from the outside, left uncovered by the mask is marked on a printed scale along one side of the sector boundary. With the mask fixed at such a position that gives a convenient count of up to 20 colonies, note is taken of the number of peripheral grooves from the printed scale and the colonies are counted at several positions of the agar plate. From the mean and the number of grooves on a standard table, the count/ml is derived.

The construction of this table, which could well take the form of a slide rule or of a programmed microprocessor, is based on equation (1):

$$\frac{X}{Y} \times \frac{1.6355 \times 10^9}{Z} \qquad (1)$$

where:

Y is the inoculum units received by the counted area;
X is the number of colonies counted; and
Z is the inoculum size ($\mu l$)

The calculation of Y is made as follows:

Any inoculum spread along the 1200 cm spiral, over 80 grooves, (and this is decided by the capacity of the microsyringe), reduces from the centre to the periphery in a geometric progression. The first term of the progression, i.e. the outermost groove, receives 1 inoculum unit whereas the 80th term, i.e. the central groove, receives 10,000 units; the difference is 4 log cycles.

Therefore, the inoculum received by any number of grooves from the periphery towards the centre of the plate can be calculated by the equation (2):

$$S_n = \frac{a(r^n - 1)}{r - 1} \qquad (2)$$

where:

$S_n$ = the total inoculum units over the 80 grooves;
a = the inoculum units received by the outermost groove;
n = total number of grooves, i.e. 80; and
r = the constant factor, i.e., $10^b$, where $$b = \frac{4 \text{ (logs)}}{80}$$

Having obtained the total inoculum units over a number of grooves in a 20° sector from a table based on equation (2), application of equation (1) gives the construction of the reference table that gives the count/ml from the number of grooves and the number of colonies counted over these grooves.

When counting involves more than 60 spirals, the whole 20° sector or the whole plate is counted.

In this way, counting can be made, without dilution of microbial suspensions in the range $5-10 \times 10^8$ cells/ml down to 60 cells/ml, when a 0.05 $\mu l$ microsyringe is used. The accuracy of counting was very high in pilot experiments, where dilutions between $10^0$ to $10^{-6}$ were used. Counting of such dilutions gave, after multiplying with the dilution factors, readings around $5 \times 10^8$/ml that differed at most by a factor of two.

In the system already described, the inoculum is delivered along the spiral track on the surface of the agar medium, e.g. in the course of 80 revolutions that give a total spiral length 1200 cm. The continuous reduction of the inoculum per unit length of spiral is controlled by the curve or Archimedes spiral, so that the amount of inoculum deposited is related logarithmically to the time of inoculation. Thus, the number of cells, and of subsequent colonies, per unit track length is progressively reduced. The degree of effective reduction, i.e. the number of log cycles difference between the first (central) groove and the peripheral groove depends on the total track length and this depends on the fineness of the inoculator tip.

In a modification of this system, the same effect is achieved but the continuous reduction of inoculum is not essential. In an embodiment of this modification, the inoculum is delivered uniformly over e.g. four areas, i.e. four 20-groove zones of the plate, but the total inoculum per zone is of logarithmic relationship, i.e. 20, 2, 0.2, 0.02 $\mu$l. or the plunger of the syringe is depressed by e.g. 12, 1.2, 0.12, 0.012 mm respectively. This can be obtained by the mechanism illustrated in FIG. 7.

Figure 7:
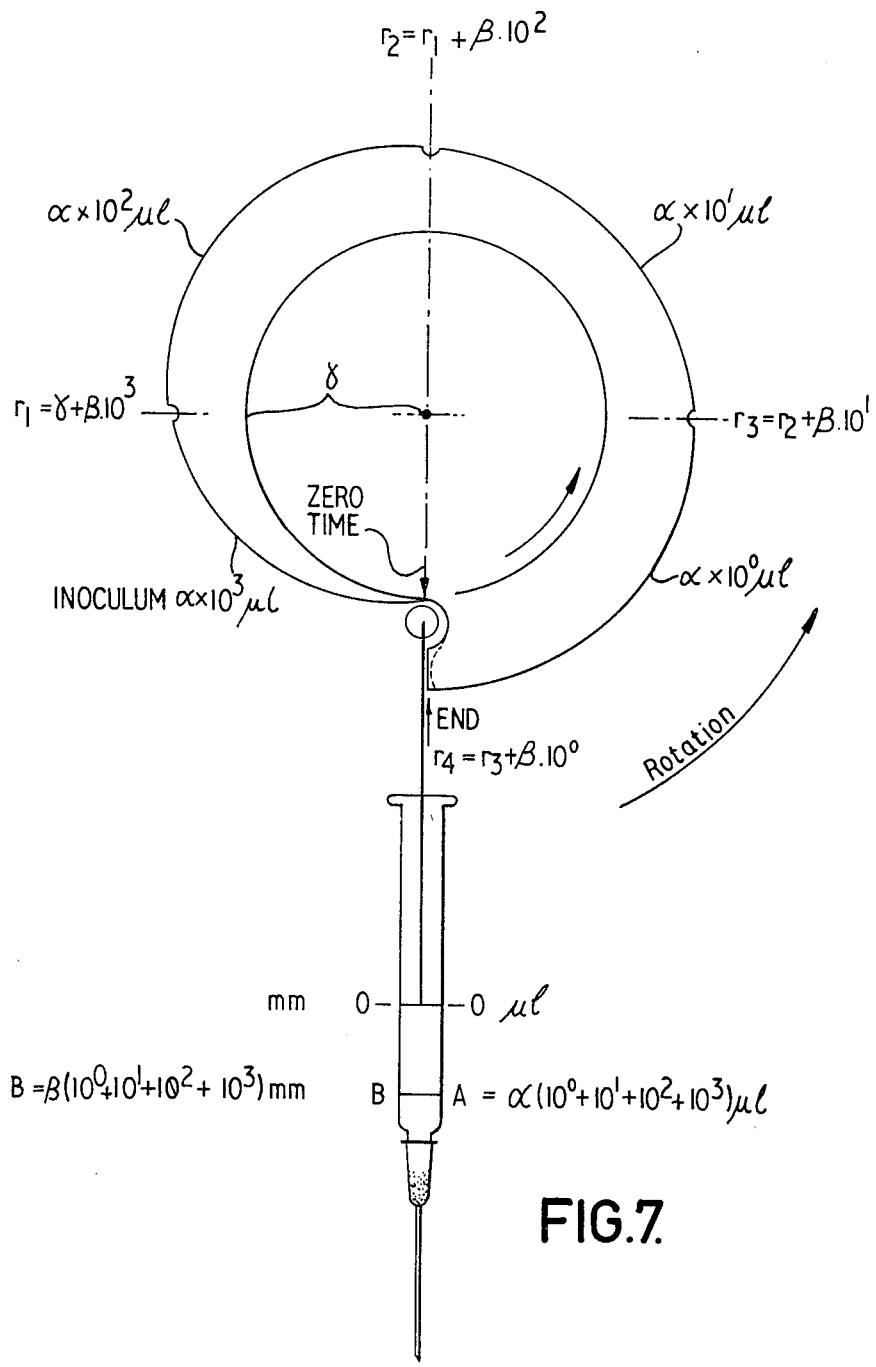
FIG. 7 shows a further possible mechanism for operation of the microsyringe.

In FIG. 7, a ball bearing at the end of the plunger (spring-loaded) maintains contact with a disc revolving in synchrony with the inoculator. Each quarter of the periphery of the disc is an Archimedes spiral ($r=\theta$), where $\gamma$ is the radius at zero time and $\beta$ is 0.012 mm of the above example. Accordingly, the inoculum that each 20-groove area receives will be as indicated in the drawing, where $\alpha$ is 0.02 $\mu$l of the above example.

At the end of a complete revolution of the disc, the plunger will return to the zero time point. The mechanism does not require reversion. The indentations at the quarter boundaries of the disc temporarily discontinue the inoculation so that the inoculator tip "cleans" itself along one or two spirals before it starts delivering a 10-fold smaller inoculum. For simplicity, the syringe in FIG. 7 is shown connected directly to the hypodermic needle. However, it is also possible to have the intermediary valves and the vial as shown in FIG. 4.

This system can easily give counts up to $10^7$ cells/ml. If, however, the last quarter of the disc is a logarithmic spiral log $r=\theta$, instead of $r=\theta$, the resolution can be up to $10^8$ cells/ml. This latter value is slightly lower than the counting efficiency of the apparatus of FIGS. 1 to 4.

Figure 8:
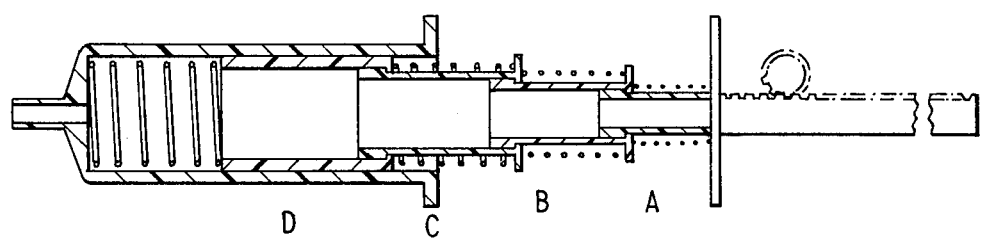
FIG. 8 shows a telescopic syringe plunger which can be used in the invention.

In the above modification, the inoculum is delivered uniformly over four areas each made up of 20 grooves of the total spiral. This effect can also be achieved by using a telescopic syringe plunger, for example as shown in FIG. 8. Four components A, B, C and D of a telescopic plunger are successively depressed at a constant rate. The plunger components are spring-loaded so that the movement always follows the order A, B, C, D. The plungers are actuated by a toothed wheel rotating in synchrony with the rotating table 2 which carries the agar plate. The toothed wheel engages with a rack in line with the plungers and, when it ceases to drive the rack, a release mechanism returns it, and the plunger components to their zero time position. As an example, a total 25 microliters of inoculum can be dispensed with a journey for each piston of 4.5 mm, the diameters of the pistons being: D 4.75 mm, C, 1.50 mm, B 0.50 mm, and A 0.15 mm.

A further embodiment of apparatus for actuating the microsyringe in synchrony with rotation of the agar plate and movement of the inoculator will now be described with reference to FIGS. 9 and 10. The inoculum dosing is controlled by a circular cam 44 similar to that of FIG. 7. The peripheral contour of the cam 44 is in contact with a roller 45 at the end of the plunger 23 of the microsyringe 5 so that, when the cam 44 rotates, the rate of depression of the plunger is dictated by its shape. The computer-drawn peripheral shape of the cam is such as to decrease the size of inoculum between the beginning and end of one revolution by a factor of $10^4$.

The connection of the syringe with the inoculator, the inoculator itself, its suspension and magnet influenced operation are as already described.

Figure 9:
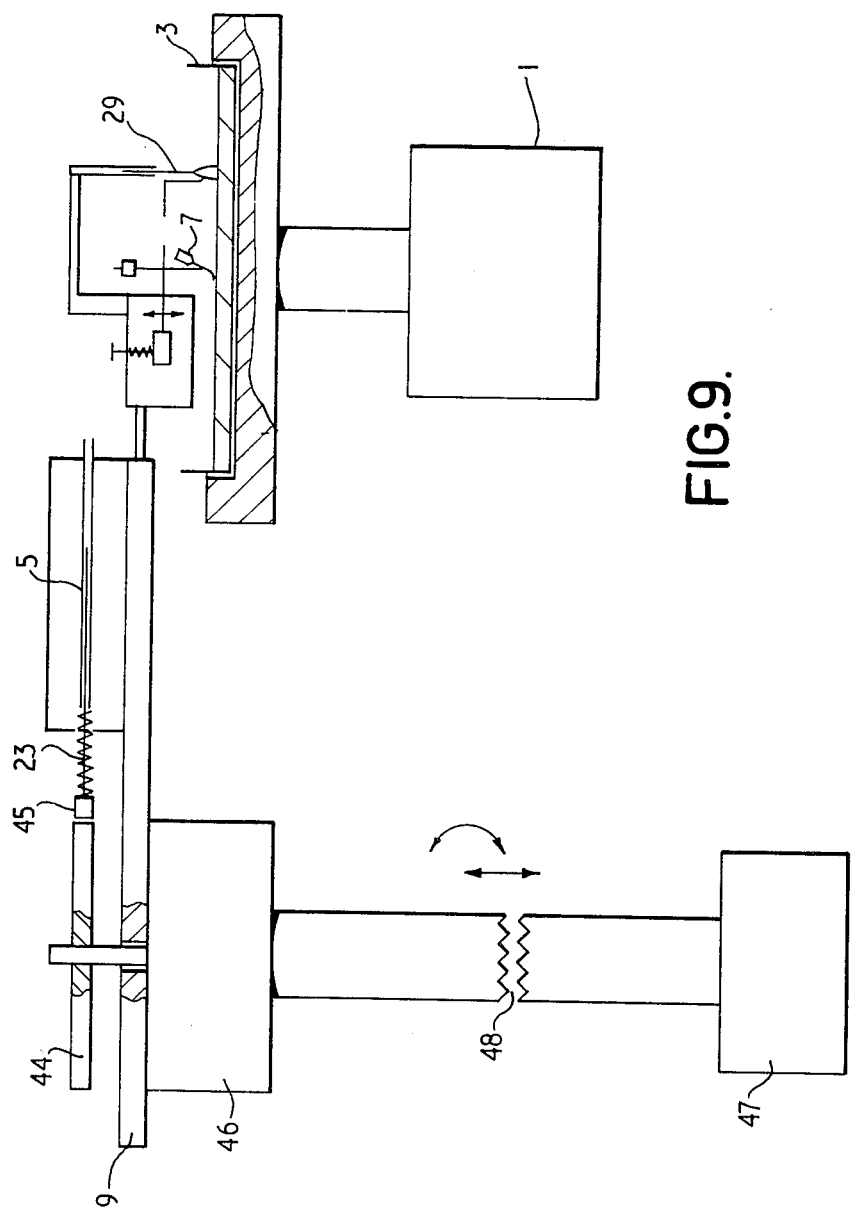
FIG. 9 is a side view of a further embodiment of spiral plating apparatus according to the invention.
Figure 10:
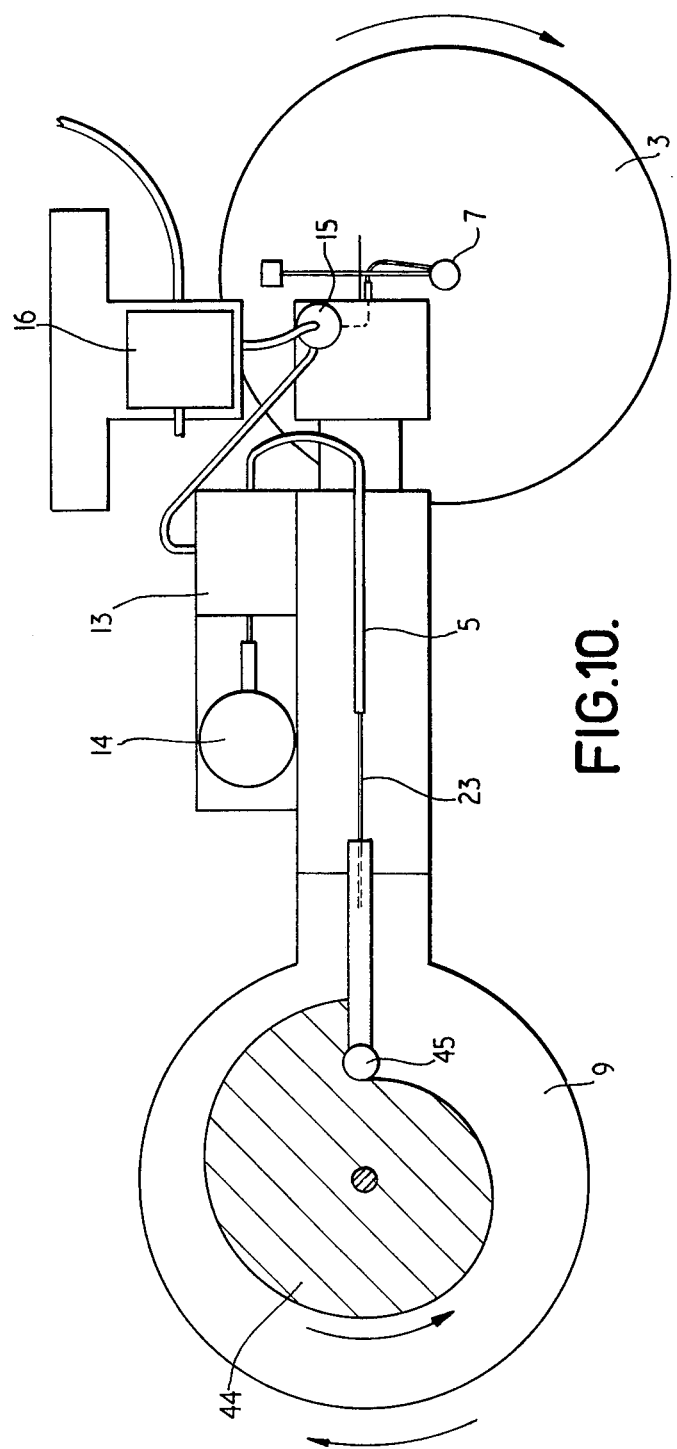
FIG. 10 is an overview of the apparatus shown in FIG. 9.

The whole syringe-inoculator assembly, including the oil reservoir, vial, and two 3-way valves shown in FIGS. 1 and 4, rests on the turning arm (mobile stage 9) of FIG. 9 and 10. The mobile stage 9 is firmly fixed on the casing of a motor 46, which turns the cam 44 at 1 r.p.m. The motor 46 is seated on the spindle of a motor 47 (2.4 rph). The function of the latter is to turn the mobile stage 9 so that the inoculator describes an arc defined by a 32 mm radius of the agar plate. On completion of this journey by the inoculator, the agar plate will have made 80 rotations (motor 1, 80 rpm) and a spiral track, much like a gramophone record, of about 1200 cm length and 80 grooves, 0.4 mm apart will have been described. During this operation, the cam 44 will have completed one revolution and a final depression of the syringe plunger by 2 cm (19.998 mm), thereby expelling a predetermined amount of inoculum. The size of inoculum is determined by the capacity of microsyringe chosen. This makes the instrument more versatile in different fields of use. A catch and release mechanism 48 (FIG. 9) disengages the stage 9 from motor 47, so that it can be manually lifted, returned to the starting position, stay high for disinfection and loading, and then be lowered and positioned on the agar plate. Precision in positioning is essential and this is achieved by means of the surface sensor assembly and the height adjustment of the inoculator shown in FIG. 3.

All three motors 1, 46 and 47 operate in synchrony, although at varying speeds, by means of a stop switch which is activated by the turning stage when reaching its terminal position. A relay switch cancels the "ON" action when the stage returns to its starting position and the switch is released when a push-button switch is pressed in order to set the system in action for the next plating. Counting of plates is as already described.

The apparatus described above with reference to the drawings incorporates a number of advantageous features in comparison with previously proposed apparatus. Performance can be compared in terms of: (a) sensitivity, (b) reproducibility, and (c) range of cell numbers over which the instrument can be reliably used. The determining factors of these are: (1) the length of the spiral, (2) the microsyringe used, and (3) the inoculator design and function.

According to a preferred embodiment of the present invention, the spiral length is 1200 cm, comprising 80 grooves spaced 0.4 mm apart. With previous apparatus, the spiral length is 150 cm, comprising about 15 grooves each about 1 mm wide and spaced about 1.5 mm apart (centre to centre). This difference does not just depend on the screw 8 driving the mobile stage 9, as this could easily be altered. Instead, it mainly results from the fineness of the inoculator tip and the stability of the inoculator in relation to the angle it forms with the surface of the medium.

In an embodiment of the invention, the microsyringe is a preferred gas-tight metal syringe designed and made specially for the purpose of this invention, of a capacity that can range from 15 microliters upwards per journey (constant) of the plunger. The capacity depends on the internal diameter of the metal tube chosen, so that the size of inoculum released suits special purposes on fitting the appropriate syringe size.

Figure 11:
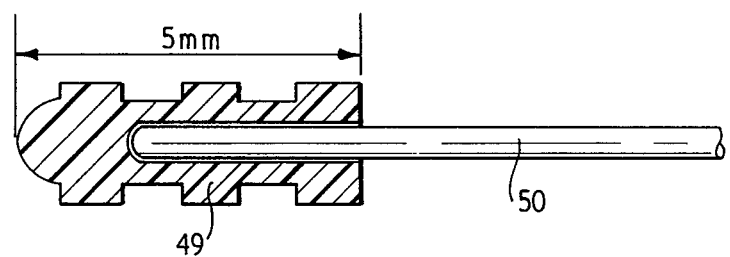
FIG. 11 shows a preferred type of metal syringe which can be used in the invention.

For the construction of the gas-tight plunger, which is a teflon tip 49 fixed on a length of wire 50, a block of teflon was turned to a 5 mm shape shown in FIG. 11. Besides the flexibility in terms of inoculum size offered by a series of such syringes, an added advantage is their durability and the better fitting of the tip along the journey of plunger as compared to glass syringes.

With the previous apparatus, a 1 ml syringe having a plunger journey of about 2 mm is used. A change to a 0.05 ml syringe would be impossible for design reasons, because the inoculum size is fixed, as opposed to the variability possible in the present invention.

The inoculator of previously proposed apparatus is the end of Teflon tubing coming from the syringe. It is allowed to rest on the agar medium at an angle of 45° or less. Its tip is therefore eliptical and its major axis is longitudinal relative to the spiral path. The finest tubing available has an internal diameter of 0.3 mm and an outside diameter of 0.7 mm. This smears the inoculum along a track at least 1 mm wide. Because of the use of such a tip, a constant quantity of medium has to be poured on to the agar plates, and the medium surface must be smooth and level. This requires extra work and skill. The normal practice in microbiology is to place plates on a bench and pour unspecified amounts of agar. These plates are then subjected to a surface drying process (for easy absorption of inoculum) which results in a more or less wrinkled agar surface. Storage of plates has the same effect. However, this wrinkled surface is detrimental to the performance of the known apparatus because the tube tip jumps over the agar irregularities, resulting in a poor inoculation pattern. The nondeposited inoculum will accumulate at the tip and be deposited subsequently along the spiral track thereby affecting the precision of plating. If the surface is left insufficiently dry, then absorption of inoculum takes a long time and may therefore result in a loss of the quantitative gradient of inoculum, i.e. the principle of the method. The medium also has to be of constant thickness in order to avoid a variable initiation radius.

In an embodiment of the present invention, the inoculator tip is that of a hypodermic needle having its pointed end cut off, with an internal diameter of 0.1 mm and an outside diameter of 0.4 mm. The actual width of groove made by the tip is of the order of 0.05 mm, which is the actual contact area with the medium. The tip will continuously follow the contours of even an over-wrinkled agar surface. This is achieved by the fineness of the inoculator tip, the skiing mechanism by which scratching of the medium is avoided and the continuing repulsion of the pair of magnets. This action does not allow the tip to become separated from the medium at any time.

The apparatus of the present invention is independent of (a) the thickness of the medium, (b) the levelling of the medium, and (c) the degree of surface drying. It shows high sensitivity with respect to distribution of the inoculum. The fine structure of the inoculator excludes carry-over of inoculum. The range over which it can be used without dilution is: a maximum of $5-10 \times 10^8$ cells/ml, and a minimum of 60 cells/ml.

Figure 12:
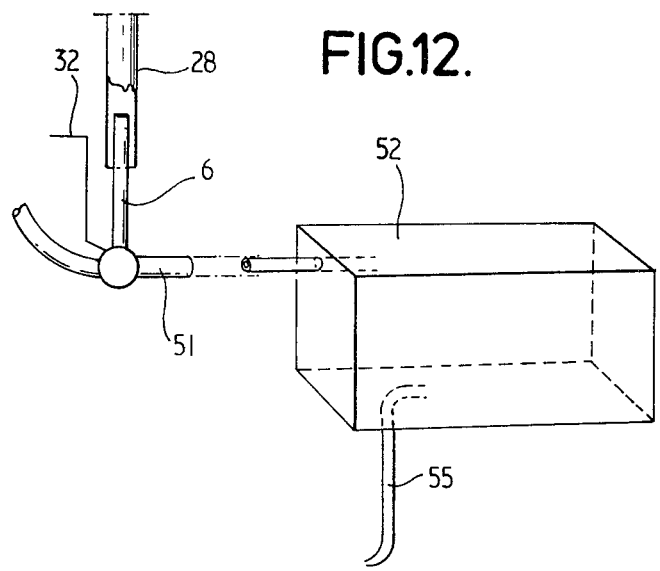
FIG. 12 shows an alternative form of inoculator assembly.
Figure 13:
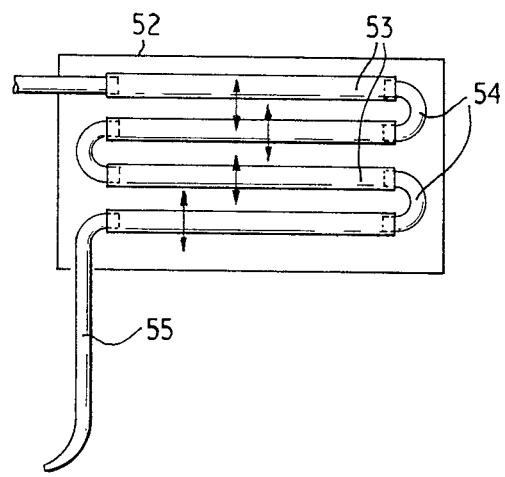
FIG. 13 shows, in section, part of the assembly of FIG. 12.

FIG. 12 shows an alternative form of inoculator assembly and FIG. 13 shows, in section, part of the assembly of FIG. 12. This modified inoculator does not utilise a pivoted balancing arm or magnetic repulsive action. The inoculator holder 6 is adjustable within a sleeve 28 and incorporates a height indicator 32 as described above. A tube 51 leads from the vial 15 as in other embodiments. The tube 51 is fixed into a hole in the side of a cartridge 52, which is supported by means of the tube 51 so that it is vertically adjustable together with the inoculator holder. Inside the cartridge, there is a zig-zag arrangement of straight plastics tubes 53 joined by 180° curved metal tubes 54. This tubing arrangement has one end fixed and another end free to flex and communicating with the inoculator needle 55. The inoculator needle passes through an oversize hole in the bottom of the cartridge. The plastics tubes 53 are rigid with respect to their diameter but can flex slightly. They therefore act as spring means (arrows show the spring action) which bias the tip of the inoculator needle towards the growth medium. The end of the plastics tubing communicating with the inoculator needle can flex up and down. Sufficient lengths of plastics tubing provide the required degree of flexibility. Alternatively, the lengths of plastics and metal tubing 53 and 54 can be replaced by a helical length of plastics tubing, having sufficient turns to provide the required spring action. The spring action within the cartridge responds towards any vertical movement of the inoculator needle, enabling the latter to ski over the surface of the growth medium.

I claim:

1. An inoculator assembly for use in a spiral plating apparatus, comprising an inoculator holder; a pivot on said inoculator holder; an arm mounted to balance on said pivot; an inoculator mounted on said arm and adapted to pass over a growth medium to be inoculated, the inoculator including a fine hollow needle through which inoculum can be dispensed, and the needle having a curved tip which can ski over the surface of the growth medium without penetrating it; and means separate from said arm for exerting a force on said inoculator such that the curved tip of the needle thereof can continuously keep contact with and follow contours on said growth medium.

2. An inoculator assembly according to claim 1, wherein said means for exerting a force comprises a magnet mounted on said inoculator holder, said magnet cooperating with a magnet mounted on said arm to produce said force.

3. An inoculator assembly according to claim 2, wherein said magnets are mounted to repel each other.

4. An inoculator assembly according to claim 1, wherein said fine hollow needle is a hypodermic needle, wherein said curved tip is adapted to contact said growth medium, and wherein said hypodermic needle has a reservoir in continuous liquid communication with a syringe, whereby actuation of said syringe causes inoculum to be expelled from said hypodermic needle.

5. An inoculator assembly according to claim 4, wherein said reservoir communicates with said syringe through a vial, and wherein said continuous liquid communication is provided by inert immiscible liquid within said syringe and between said syringe and said vial.

6. An inoculator assembly according to claim 1, wherein said means for exerting a force on said inoculator comprises spring means adapted to bias said inoculator towards said growth medium.

7. An inoculator assembly according to claim 6, wherein said spring means comprises flexible tubing having one end fixed and another end free to flex and communicating with said inoculator.

8. Apparatus for spiral plating of microorganisms on a growth medium for making a viable cell count, which comprises a source of inoculum; means for rotating a plate containing growth medium; an inoculator adapted to expel inoculum onto said growth medium, the inoculator including a fine hollow needle through which inoculum can be dispensed, and the needle having a curved tip which can ski over the surface of the growth medium without penetrating it; means for moving said inoculator along a radius of said plate as said plate rotates so as to deposit inoculum along a spiral path on said growth medium; means separate from of said arm for exerting a force on said inoculator such that the curved tip of the needle thereof can continuously keep contact with and follow contours on said growth medium; and means for controllably varying the rate of expulsion of inoculum along said spiral path.

9. Apparatus according to claim 8, also comprising an inoculator holder, a pivot on said inoculator holder, and an arm mounted to balance on said pivot, said inoculator being mounted on said arm and adapted to pass over said growth medium to be inoculated.

10. Apparatus according to claim 9, wherein said means for exerting a force comprises a magnet mounted on said inoculator holder, said magnet cooperating with a magnet mounted on said arm to produce said force.

11. Apparatus according to claim 10, wherein said magnets are mounted to repel each other.

12. Apparatus according to claim 8, wherein said inoculator is in continuous liquid communication with a syringe, whereby actuation of said syringe causes inoculum to be expelled from said inoculator.

13. Apparatus according to claim 12, wherein said inoculator communicates with said syringe through a vial, and wherein said continuous liquid communication is provided by inert immiscible liquid within said syringe and between said syringe and said vial.

14. Apparatus according to claim 12, wherein said means for controllably varying the rate of expulsion of inoculum along said spiral path comprises a rotatable member having a curved surface in driving engagement with the plunger of said syringe, and means for rotating said rotatable member whereby said plunger is depressed at a rate varying according to the curvature of said curved surface.

15. Apparatus according to claim 14, wherein said curvature is such that the rate of expulsion of inoculum continuously varies along said spiral path in a logarithmic relationship.

16. Apparatus according to claim 8, wherein said means for exerting a force on said inoculator comprises spring means adapted to bias said inoculator towards said growth medium.

17. Apparatus according to claim 16, wherein said spring means comprises flexible tubing having one end fixed and another end free to flex and communicating with said inoculator.

18. A surface sensor assembly for use in a spiral plating apparatus, comprising a probe adjustable in height, an inoculator holder adjustable in height, and a pair of indicators respectively on said probe and on said inoculator holder arranged so that, when said probe is adjusted to contact a growth medium, and said inoculator holder is adjusted until said indicators are in a predetermined relative position, said inoculator holder is then at a suitable height for inoculum to be distributed on said growth medium.

19. A surface sensor assembly according to claim 18, wherein said probe and said inoculator holder each comprise a rod vertically slidable within a respective fixed vertical sleeve.

20. A surface sensor assembly according to claim 18, wherein said inoculator holder carries an inoculator which is movable between a non-operative and an operative position, said non-operative position being adopted during vertical adjustment.

* * * * *